United States Patent
Sakaguchi et al.

(10) Patent No.: US 10,307,565 B2
(45) Date of Patent: Jun. 4, 2019

(54) ACCOMMODATION TOOL

(71) Applicant: TERUMO KABUSHIKI KAISHA, Shibuya-ku, Tokyo (JP)

(72) Inventors: Yuuki Sakaguchi, Shizuoka (JP); Yushin Yazaki, Kanagawa (JP); Jo Fujiki, Shizuoka (JP); Takito Inukai, Shizuoka (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 0 days.

(21) Appl. No.: 15/631,107

(22) Filed: Jun. 23, 2017

(65) Prior Publication Data

US 2017/0281902 A1  Oct. 5, 2017

Related U.S. Application Data

(63) Continuation of application No. PCT/JP2016/051026, filed on Jan. 14, 2016.

(30) Foreign Application Priority Data

Jan. 16, 2015 (JP) .................................. 2015-007201

(51) Int. Cl.
*A61M 25/00* (2006.01)
*A61B 50/00* (2016.01)
(Continued)

(52) U.S. Cl.
CPC ............ *A61M 25/002* (2013.01); *A61B 50/00* (2016.02); *A61B 50/20* (2016.02); *A61B 50/30* (2016.02);
(Continued)

(58) Field of Classification Search
CPC .. A61M 25/00; A61M 25/001; A61M 25/002; A61M 25/09; A61B 5/00;
(Continued)

(56) References Cited

U.S. PATENT DOCUMENTS 2,938,624 A * 5/1960 Runkel ............ A61B 17/06123
206/63.3
4,721,123 A    1/1988 Cosentino et al.
(Continued)

FOREIGN PATENT DOCUMENTS

EP       0 820 781 A1    1/1998
JP     2004-524912 A    8/2004
(Continued)

OTHER PUBLICATIONS

International Search Report (PCT/ISA/210) dated Apr. 19, 2016, by the Japanese Patent Office as the International Searching Authority for International Application No. PCT/JP2016/051026.
(Continued)

*Primary Examiner* — Bryon P Gehman
(74) *Attorney, Agent, or Firm* — Buchanan Ingersoll & Rooney PC

(57) ABSTRACT

An accommodation tool is disclosed with which an operator can easily wind and accommodate a flexible medical elongated body. An accommodation tool winds and accommodates the flexible medical elongated body, for example, a guide wire. The accommodation tool has an inner wall, an outer wall, and an interlock wall. The guide wire is wound around the inner wall. The outer wall defines an accommodation space for accommodating the guide wire between the inner wall and the outer wall, and that is disposed further outward in a radial direction from a centroid of the accommodation tool than the inner wall. The interlock wall interlocks one end portion of the inner wall and one end portion of the outer wall with each other.

20 Claims, 8 Drawing Sheets

(51) Int. Cl.
*A61B 50/30* (2016.01)
*A61B 50/20* (2016.01)
*A61M 25/09* (2006.01)
*B65D 85/04* (2006.01)

(52) U.S. Cl.
CPC ............. *A61M 25/00* (2013.01); *A61M 25/09* (2013.01); *B65D 85/04* (2013.01)

(58) Field of Classification Search
CPC ......... A61B 50/00; A61B 50/20; A61B 50/30; B65D 83/08; B65D 83/0847; B65D 83/10; B65D 83/20; B65D 85/04; B65D 85/672
USPC .............. 206/63.3, 363, 364, 438; 211/85.13
See application file for complete search history.

(56) References Cited

U.S. PATENT DOCUMENTS

| | | | | |
|---|---|---|---|---|
| 6,547,072 B2* | 4/2003 | Whiting | ............. | A61M 25/002 206/364 |
| 6,719,135 B2* | 4/2004 | Armijo | ............... | A61M 25/002 206/364 |
| 6,902,057 B2* | 6/2005 | Duffy | ................... | A61M 25/002 206/364 |
| 7,766,162 B2* | 8/2010 | Maki | ................... | A61M 25/002 206/364 |
| 8,002,113 B1* | 8/2011 | Cummings | .......... | B65D 85/672 206/438 |
| 9,744,333 B2* | 8/2017 | Terzibashian | ....... | A61M 25/002 |
| 2004/0087966 A1* | 5/2004 | McDevitt | ........ | A61M 25/09041 606/108 |

FOREIGN PATENT DOCUMENTS

WO  WO 0178824 A1 * 10/2001 .......... A61M 25/002
WO  WO 02/074379 A1   9/2002

OTHER PUBLICATIONS

Written Opinion (PCT/ISA/237) dated Apr. 19, 2016, by the Japanese Patent Office as the International Searching Authority for International Application No. PCT/JP2016/051026.

* cited by examiner

ACCOMMODATION TOOL

CROSS-REFERENCES TO RELATED APPLICATIONS

This application is a continuation of International Application No. PCT/JP2016/051026 filed on Jan. 14, 2016, which claims priority to Japanese Application No. 2015-007201 filed on Jan. 16, 2015, the entire contents of which are incorporated herein by reference.

TECHNICAL FIELD

The present disclosure relates to an accommodation tool which winds and accommodates a flexible medical elongated body.

BACKGROUND ART

In the related art, until a health care worker (operator) uses a medical elongated body such as a guide wire, the medical elongated body is soaked in a container such as a vat filled with a physiological salt solution. In this case, in order to prevent physical damage or to improve operability, the medical elongated body is generally stored in a state where the medical elongated body is wound and accommodated in an accommodation tool such as a holder.

For example, until the health care worker (for example, the operator) introduces the guide wire again into a living body after removing the guide wire once from the inside of the living body, the guide wire maintains a wet state after the guide wire is soaked in the physiological salt solution filling the container such as the vat.

U.S. Pat. No. 6,547,072 discloses a guide wire holder, which accommodates the guide wire after the guide wire is wound once in a coil shape.

In addition, U.S. Pat. No. 6,902,057 discloses a catheter holder, which includes a luer holding portion for fixing a proximal portion of the medical elongated body such as a catheter to a portion of an outer wall, and a holding portion for preventing the accommodated catheter from being untied.

However, in a case of the holder as disclosed in U.S. Pat. No. 6,547,072, when the holder accommodates the medical elongated body, the operator has to manually wind the medical elongated body by aligning the medical elongated body with a shape of the holder. Consequently, it takes time and effort when in use.

In addition, even in a case of the holder as disclosed in U.S. Pat. No. 6,902,057, when the holder accommodates the medical elongated body, the operator has to wind the medical elongated body by aligning the medical elongated body with various holding portions of the holder. Consequently, it takes time and effort similarly to a case of using the holder as disclosed in U.S. Pat. No. 6,547,072.

SUMMARY OF INVENTION

An accommodation tool is disclosed with which an operator can easily wind and accommodate a flexible medical elongated body.

An accommodation tool is disclosed, which winds and accommodates a flexible medical elongated body. The accommodation tool has an inner wall around which the medical elongated body is wound, an outer wall that defines an accommodation space for accommodating the medical elongated body between the inner wall and the outer wall, and that is disposed further outward in a radial direction from a centroid of the accommodation tool than the inner wall, and an interlock wall that interlocks one end portion of the inner wall and one end portion of the outer wall with each other. The other end portion of the inner wall extending from one end portion of the inner wall extends in a stretching direction intersecting the radial direction so as to be longer than the other end portion of the outer wall extending from one end portion of the outer wall, and tilts toward the outer wall.

According to the accommodation tool of the present disclosure, the other end portion of the inner wall extending from one end portion of the inner wall extends in the stretching direction intersecting the radial direction from the centroid of the accommodation tool so as to be longer than the other end portion of the outer wall extending from one end portion of the outer wall, and tilts toward the outer wall. According to this configuration, in a case where an operator winds the medical elongated body from the other end portion side of the inner wall, the operator can wind the medical elongated body around the other end portion of the inner wall without interfering with the other end portion of the outer wall. In addition, when the medical elongated body is wound around the other end portion of the inner wall, in the medical elongated body, an arc formed along a circumferential direction decreases due to a tensile force of the operator. After the medical elongated body is moved from the other end portion side of the inner wall to one end portion side of the inner wall, an elastic force causes the medical elongated body to return to the original position from a state where the medical elongated body is wound. In this manner, the arc formed along the circumferential direction increases, and the medical elongated body is guided to the outer wall side. Therefore, the operator can relatively easily wind and accommodate the flexible medical elongated body in the accommodation tool. In addition, when the medical elongated body is pulled out from the accommodation tool according to the present disclosure, the medical elongated body gradually moves close to the inner wall due to tension generated in the medical elongated body. In this manner, the medical elongated body can be relatively easily pulled out from the accommodation tool without becoming entangled inside the accommodation tool. In addition, in a case where a plurality of medical elongated bodies is accommodated in the accommodation tool, the same advantageous effect can also be expected. Note that, the description of the radial direction and outward in the radial direction means a direction toward the inner wall side or the outer wall side from the centroid of the accommodation tool. Here, the description of "the outer wall disposed further outward in the radial direction than the inner wall" represents that the outer wall is disposed at a position where the outer wall is further separated from the centroid of the accommodation tool than the inner wall.

In accordance with an another aspect, a method is disclosed of winding a flexible medical body around an accommodation tool, the accommodation tool including an inner wall, an outer wall that defines an accommodation space for accommodating the flexible medical elongated body between the inner wall and the outer wall, and that is disposed further outward in a radial direction from a centroid of the accommodation tool than the inner wall, and an interlock wall that interlocks one end portion of the inner wall and one end portion of the outer wall with each other, wherein the other end portion of the inner wall extending from one end portion of the inner wall extends in a stretching direction intersecting the radial direction so as to be longer than the other end portion of the outer wall extending from one end portion of the outer wall, and tilts toward the outer wall, the method comprising: winding the flexible medical elongated body around the inner wall of the accommodation tool while pulling on the flexible elongated body.

DETAILED DESCRIPTION

Figure 1A:
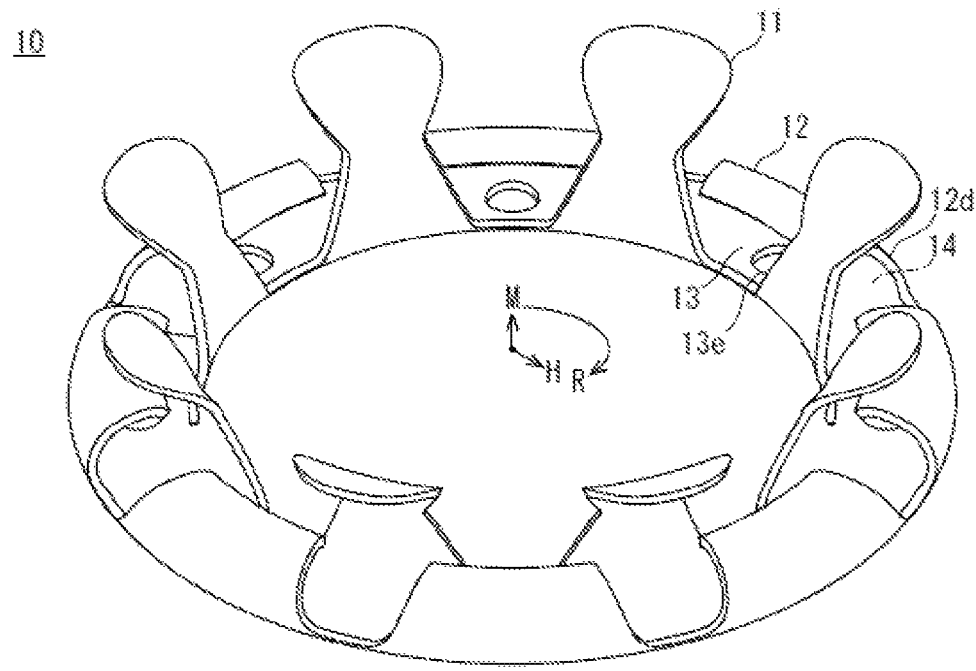
FIGS. 1A and 1B are perspective views illustrating an accommodation tool according to an exemplary embodiment.

Hereinafter, an embodiment according to the present disclosure will be described with reference to the accompanying drawings. In describing the drawings, the same reference numerals will be given to the same elements, and repeated description will be omitted. Sizes or proportions of each member in the drawings are exaggerated and different from actual sizes and proportions for convenience of description, in some cases. In all of the drawings in FIGS. 1A to 8, axes or orientations are indicated by arrows represented by the reference numerals M, H, and R. The arrow represented by the reference numeral M indicates a winding axis M of the medical elongated body. The arrow represented by the reference numeral H indicates a normal direction H intersecting the winding axis M. A direction of the arrow represented by the reference numeral R indicates a circumferential direction R in which the winding axis M is a central axis. In the medical elongated body, a side manually operated by an operator corresponds to a proximal side, and a side introduced into a living body (for example, a blood vessel) of a patient corresponds to a distal side. Note that, the winding axis M of the medical elongated body is a centroid of the accommodation tool.

Figure 2:
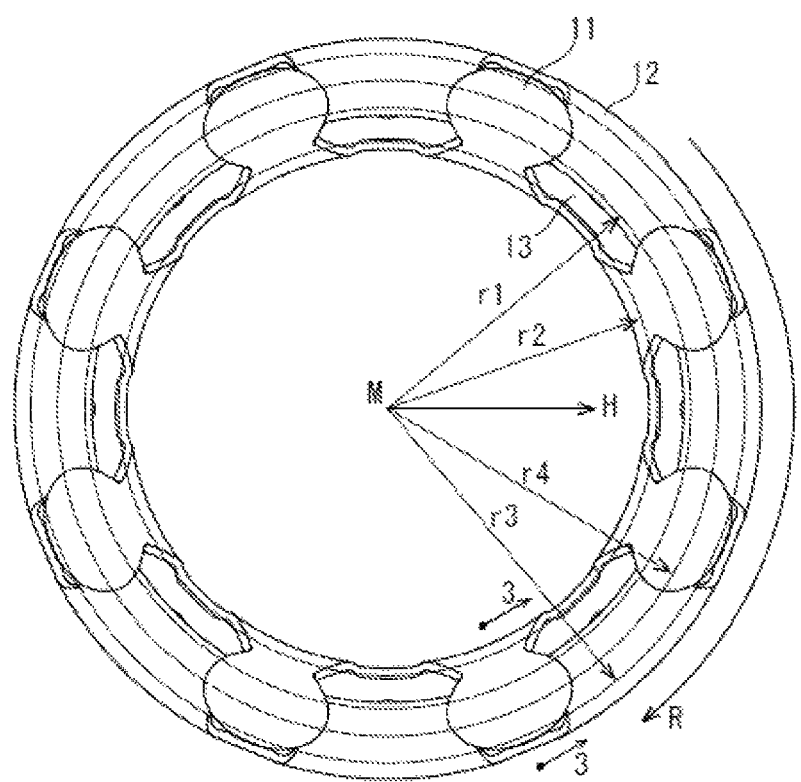
FIG. 2 is a side view illustrating a state where the accommodation tool in FIGS. 1A and 1B is oriented from one side (upper side) toward the other side (lower side) of a winding axis.
Figure 5:
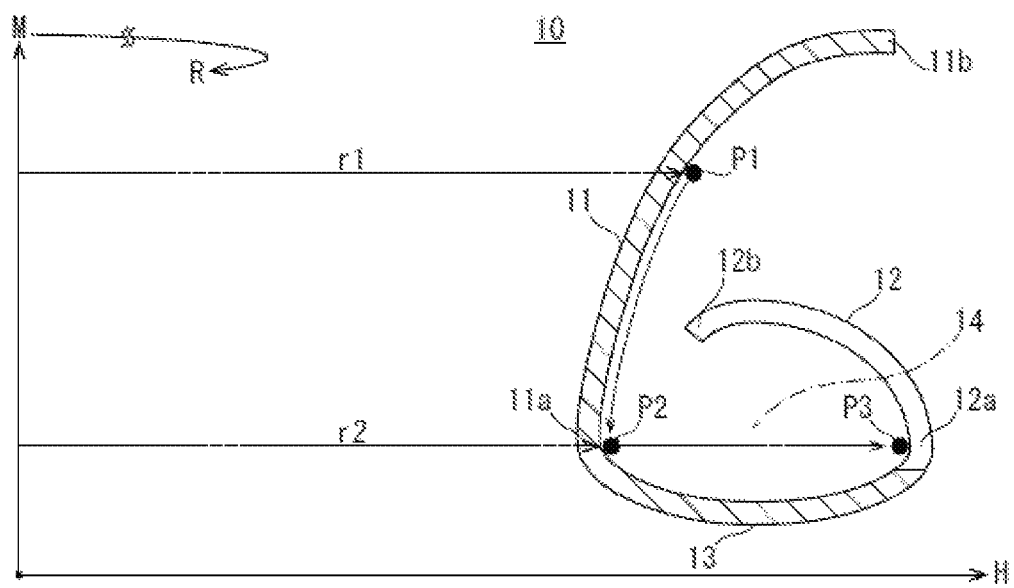
FIG. 5 is a schematic view illustrating a process of winding and accommodating the medical elongated body in the accommodation tool in FIG. 4.
Figure 8:
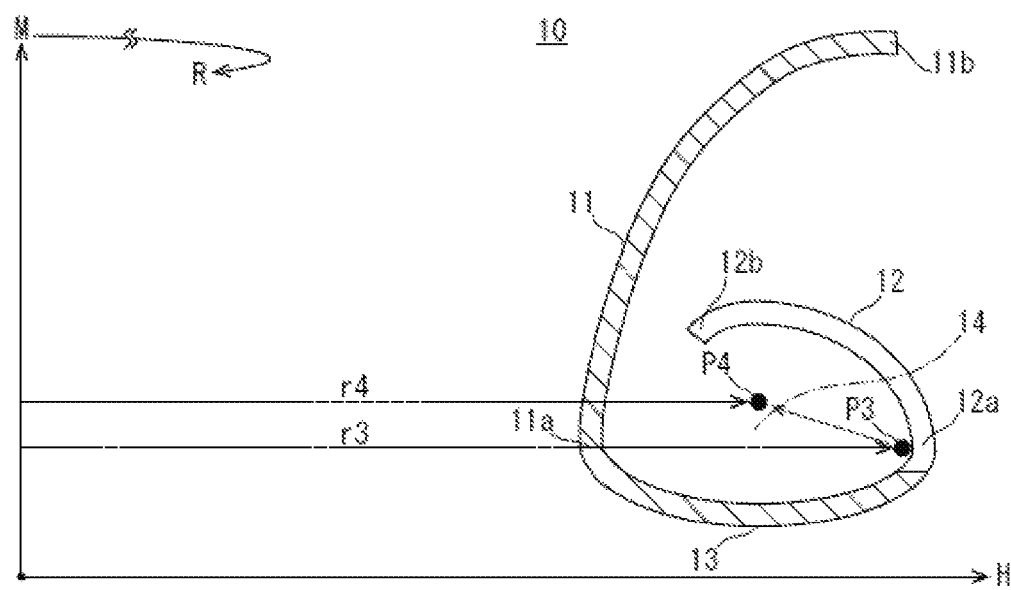
FIG. 8 is a schematic view illustrating a process of pulling out the medical elongated body from the accommodation tool in FIG. 7.

In the drawings, as illustrated in FIG. 2, arcs of a guide wire 100 to be accommodated in an accommodation tool 10 are schematically illustrated by reference numerals r1, r2, r3, and r4 corresponding to arcs formed along the circumferential direction R. The arcs r1 and r2 in FIG. 2 relate to r1 and r2, which are illustrated in FIG. 5. The arcs r3 and r4 in FIG. 2 relate to r3 and r4, which are illustrated in FIG. 8.

A configuration of the accommodation tool 10 will be described with reference to FIGS. 1A to 3.

Figure 1B:
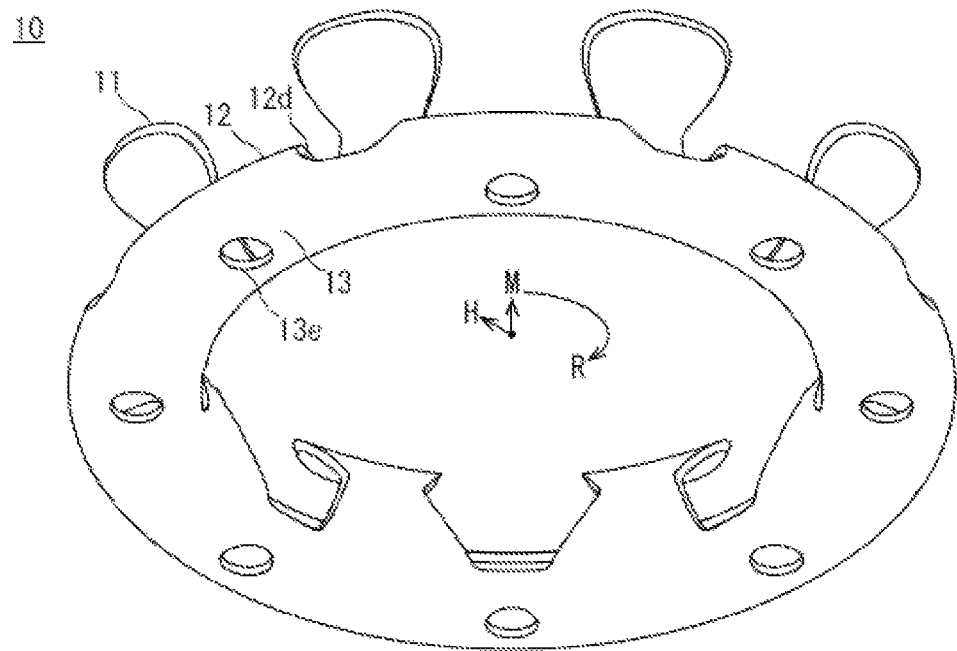
Figure 3:
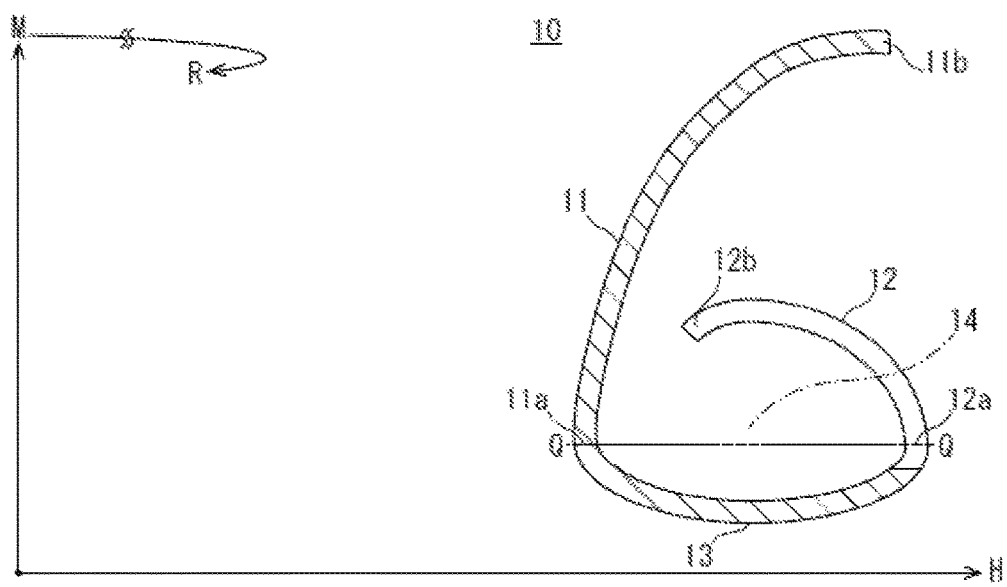
FIG. 3 is a side view illustrating a cross section of a main portion of the accommodation tool in FIGS. 1A and 1B.

FIG. 1A is a perspective view illustrating the accommodation tool 10 from above. FIG. 1B is a perspective view illustrating the accommodation tool 10 from below. FIG. 2 is a side view illustrating a state where the accommodation tool in FIGS. 1A and 1B is oriented from an upper side toward a lower side of a winding axis M. FIG. 3 is a side view illustrating a cross section of a main portion of the accommodation tool 10 in FIGS. 1A and 1B, and taken along line 3-3 in FIG. 2.

In accordance with an exemplary embodiment, the accommodation tool 10 winds and accommodates the flexible guide wire 100. As illustrated in FIGS. 1A and 1B, the accommodation tool 10 is annularly formed. An inner wall 11 and an outer wall 12 are alternately arranged on the arc formed along the circumferential direction R of the wound guide wire 100. In the accommodation tool 10, the outer wall 12 is disposed further outward in a radial direction of a circle formed by the accommodation tool 10 than the inner wall 11. Here, in the accommodation tool 10, an accommodation space 14 is defined between the inner wall 11 and the outer wall 12 as illustrated in FIG. 3.

As illustrated in FIGS. 1A, 1B, and 3, in the accommodation tool 10, on the other side (lower side) in the stretching direction intersecting the radial direction, one end portion 11a of the inner wall 11 and one end portion 12a of the outer wall 12 interlock with each other by the interlock wall 13. That is, in the accommodation tool 10, a plurality of inner walls 11, a plurality of outer walls 12, and the interlock wall 13 are integrally formed by one member. As illustrated in FIGS. 1A, 1B, and 3, on one side (upper side) in the stretching direction intersecting the radial direction, the accommodation tool 10 can introduce the guide wire 100 from a portion between the other end portion 11b of the inner wall 11 and the other end portion 12b of the outer wall 12.

In accordance with an exemplary embodiment, the guide wire 100 is wound around the inner wall 11 illustrated in FIGS. 1A to 4. The inner wall 11 extends in the stretching direction intersecting the radial direction. As illustrated in FIGS. 1A, 1B, and 2, the plurality of inner walls 11 is formed by leaving a gap therebetween along the circumferential direction R. In the inner wall 11, the other end portion 11b extending from one end portion 11a connected to the interlock wall 13 corresponding to a bottom surface of the accommodation tool 10 tilts toward the outer wall 12. Specifically, as illustrated in FIG. 3, in the inner wall 11, a wall surface from one end portion 11a to the other end portion 11b is bent inward in the radial direction in a convex shape. That is, the inner wall 11 is bent so as to swell inward in the radial direction. Since the inner wall 11 has this shape, the inner wall 11 is likely to move along the guide wire 100. Note that, the radially inward direction means a direction toward the centroid of the accommodation tool from the inner wall side or the outer wall side.

Figure 4:
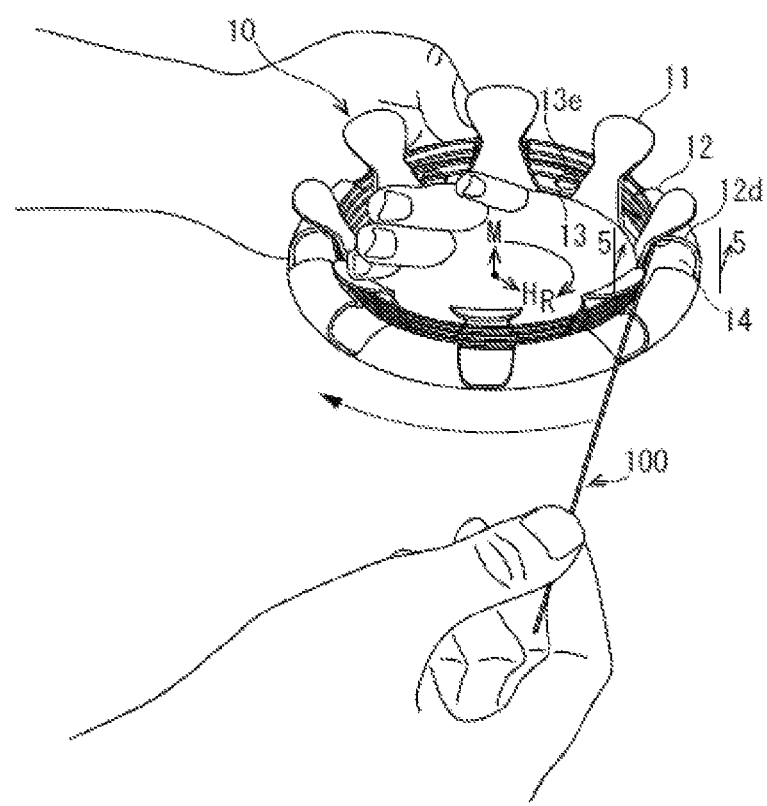
FIG. 4 is a perspective view illustrating a state where a medical elongated body is wound and accommodated in the accommodation tool in FIGS. 1A and 1B.

As illustrated in FIG. 3, the other end portion 11b of the inner wall 11 extends in the stretching direction intersecting the radial direction of the guide wire 100 wound as illustrated in FIG. 4 so to be longer than the other end portion 12b extending from one end portion 12a of the outer wall 12. That is, the other end portion 11b of the inner wall 11 further protrudes in the stretching direction intersecting the radial direction than the other end portion 12b of the outer wall 12. Furthermore, as illustrated in FIG. 3, a terminal of the other end portion 11b of the inner wall 11 is located further outward in the radial direction than a terminal of the other end portion 12b of the outer wall 12. That is, the other end portion 11b of the inner wall 11 is disposed so as to cover the other end portion 12b of the outer wall 12 in the stretching direction intersecting the radial direction.

Since the guide wire 100 is wound around the inner wall 11 in an arc shape, it is desirable that three or more inner walls 11 are formed at an equal interval along the circumferential direction R. As illustrated in FIGS. 1A and 1B, eight inner walls 11 are illustrated as an example. In accordance with an exemplary embodiment, the plurality of inner walls 11 may have the same shape, or may have mutually different shapes. A configuration may be adopted in which only one of the plurality of inner walls 11 includes a notch so as to hold an end portion (for example, a proximal side) to start winding of the guide wire 100 by inserting the end portion into the notch.

Similarly to the inner wall 11, the outer wall 12 illustrated in FIGS. 1A to 4 extends in the stretching direction intersecting the radial direction. As illustrated in FIGS. 1A and 1B, a plurality of outer walls 12 is formed by leaving a gap therebetween along the circumferential direction R so as to alternate with the inner walls 11. As illustrated in FIG. 3, in the outer wall 12, the other end portion 12b extending from one end portion 12a interlocking with the interlock wall 13 corresponding to the bottom surface of the accommodation tool 10 tilts toward the inner wall 11. Specifically, as illustrated in FIG. 3, in the outer wall 12, a wall surface from one end portion 12a to the other end portion 12b is bent outward in the radial direction in a convex shape. That is, the outer wall 12 is bent so as to swell outward in the radial direction. Since the outer wall 12 has this shape, the outer wall 12 is likely to move along the guide wire 100, similarly to the inner wall 11.

Similarly to the inner wall 11, since the outer wall 12 supports the guide wire 100 in an arc shape, it can be desirable that three or more outer walls 12 are formed at an equal interval along the circumferential direction R. As illustrated in FIGS. 1A and 1B, for example, eight outer walls 12 are illustrated as an example, similarly to the inner walls 11. The plurality of outer walls 12 may have the same shape, or may have mutually different shapes. A configuration may be adopted in which the outer wall 12 includes a notch so as to hold an end portion (for example, a distal side) to end winding of the guide wire 100 by inserting the end portion into the notch. In accordance with an exemplary embodiment, for example, if all of the outer walls 12 respectively include a notch, each end portion is likely to be held at any position along the circumferential direction R regardless of the total length of the guide wire 100. In addition, when the guide wire 100 is accommodated, the end portion to start winding of the guide wire 100 may be inserted into the notch of the outer wall 12. In this manner, since the end portion to start winding of the guide wire 100 is fixed, the guide wire 100 is likely to be wound around the inner wall 11.

In accordance with an exemplary embodiment, the interlock wall 13 extends so as to be further separated from the inner wall 11 or the outer wall 12 than a portion on a line (portion of Q-Q illustrated in FIG. 3) connecting one end portion 11a of the inner wall 11 and one end portion 12a of the outer wall 12 to each other. That is, the interlock wall 13 is formed in a concave shape with respect to the accommodation space 14 formed between the inner wall 11 and the outer wall 12. The interlock wall 13 has a through-hole 13e formed along the stretching direction intersecting the radial direction. When the accommodation tool 10 is soaked in a container such as a vat 200 filled with a physiological salt solution, the through-hole 13e expedites the physiological salt solution to permeate the accommodation space 14. In addition, when the accommodation tool 10 is removed from the container such as the vat 200 filled with the physiological salt solution, the through-hole 13e expedites the physiological salt solution to be discharged from the accommodation space 14. Therefore, the accommodation tool 10 is likely to be soaked in or to be discharged from the container such as the vat 200 filled with the physiological salt solution. Note that, in a case where the accommodation tool 10 is not soaked in the container filled with a liquid, the accommodation tool 10 may not have the through-hole 13e.

In accordance with an exemplary embodiment, as an example, the through-hole 13e has a circular shape, and eight openings are formed at an equal interval along the circumferential direction R. The through-hole 13e is formed between the inner wall 11 and the inner wall 11 which are adjacent to each other, and is formed on the interlock wall 13 so as to be covered with the outer wall 12. The through-hole 13e may be formed between the outer wall 12 and the outer wall 12 which are adjacent to each other, and may be formed on the interlock wall 13 so as to be covered with the inner wall 11.

For example, the accommodation tool 10 can be formed through molding such as injection molding using a mold, molding by means of cutting using an end mill, or molding using a three-dimensional printer. In accordance with an exemplary embodiment, the accommodation tool 10 may be formed in such a way that the plurality of inner walls 11, the plurality of outer walls 12, and the interlock wall 13 are joined to each other after being respectively formed as separate bodies. For example, the accommodation tool 10 can be formed using plastics, metal, glass, and pottery. For example, in a case where there is a possibility that the accommodation tool 10 may be soaked in liquids such as the physiological salt solution, the accommodation tool 10 employs a material, which can be inert to the liquids.

A method of using the accommodation tool 10 will be described with reference to FIGS. 4 to 8.

Figure 6:
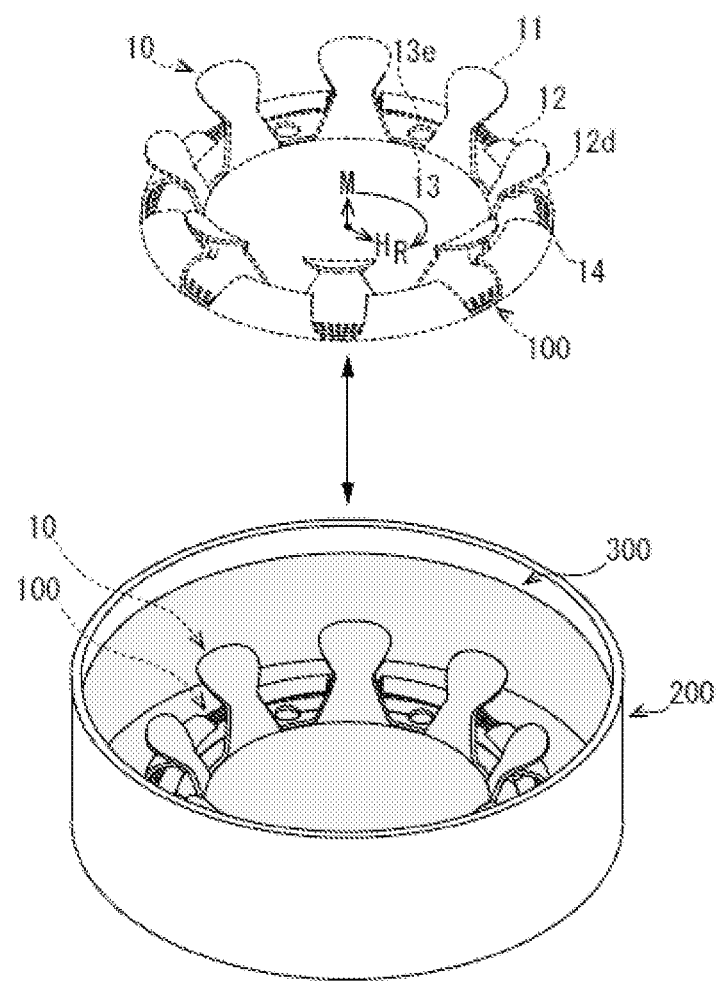
FIG. 6 is a perspective view illustrating each state before and after the medical elongated body accommodated in the accommodation tool is soaked in a physiological salt solution, subsequently from each state illustrated in FIGS. 4 and 5.
Figure 7:
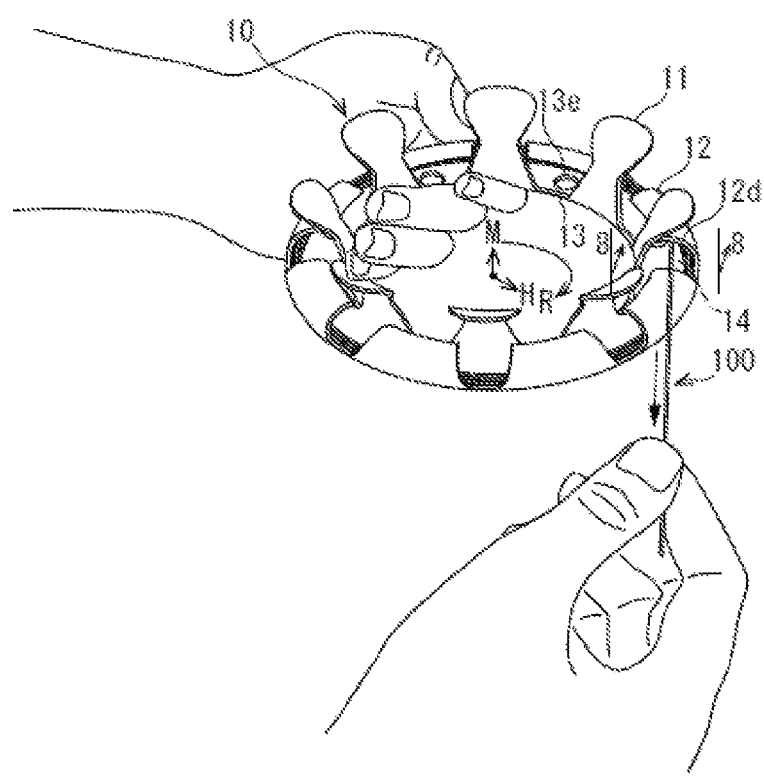
FIG. 7 is a perspective view illustrating a state where the medical elongated body is pulled out from the accommodation tool, subsequently from a state illustrated in FIG. 6.

FIG. 4 is a perspective view illustrating a state where the guide wire 100 is wound and accommodated in the accommodation tool 10 in FIGS. 1A and 1B. FIG. 5 is a schematic view illustrating a process of winding and accommodating the guide wire 100 in the accommodation tool 10 in FIG. 4. FIG. 6 is a perspective view illustrating each state before and after the guide wire 100 accommodated in the accommodation tool 10 is soaked in the physiological salt solution, subsequently from each state illustrated in FIGS. 4 and 5. FIG. 7 is a perspective view illustrating a state where the guide wire 100 is pulled out from the accommodation tool 10, subsequently from a state illustrated in FIG. 6. FIG. 8 is a schematic view illustrating a process of pulling out the guide wire 100 from the accommodation tool 10 in FIG. 7.

A method in which an operator winds and accommodates the guide wire 100 in the accommodation tool 10 will be described with reference to FIGS. 4 and 5.

For example, in a state where the operator grips the accommodation tool 10 with his or her left hand as illustrated in FIG. 4, the operator can wind the guide wire 100 around the inner wall 11 of the accommodation tool 10 while pulling the guide wire 100 with his or her right hand. Note that, when starting to wind the guide wire 100 around the accommodation tool 10, the operator pushes on an end portion (for example, a proximal side) of the guide wire 100 to start winding of the guide wire 100 with the left hand's thumb so as to prevent the movement of the end portion of the guide wire 100.

Subsequently, as illustrated in FIG. 4, the operator releases the hand from the guide wire 100 after winding the guide wire 100 around the inner wall 11 of the accommodation tool 10. The guide wire 100 released by the operator attempts to return to the original position due to an elastic force. In this manner, an arc formed along the circumferential direction R in which the winding axis M is the central axis increases, and the guide wire 100 is guided to the outer wall 12 side after being separated from the inner wall 11. According to this method, the operator winds and accommodates the guide wire 100 in the accommodation tool 10.

Here, in a state where the operator sufficiently grips the accommodation tool 10 while pushing the outer wall 12 with one hand's thumb, the operator can wind the guide wire 100 around the inner wall 11 by pinching the guide wire 100 with the other hand. That is, the accommodation tool 10 has a shape, which is likely to be gripped by the operator and in which the guide wire 100 is likely to be wound.

In this case, as illustrated in FIG. 5, the guide wire 100 is wound around a winding start position P1 (the arc of the guide wire 100 at this position corresponds to r1 in the drawing) on the other end portion 11b side of the inner wall 11 by the operator. Here, the other end portion 11b of the inner wall 11 tilts toward the outer wall 12. Accordingly, a tension component force of the guide wire 100 wound by the operator is applied from the winding start position P1 on the other end portion 11b side to an intermediate winding position P2 (the arc of the guide wire 100 at this position corresponds to r2 in the drawing, r2<r1) side on one end portion 11a side. In this manner, the guide wire 100 moves from the winding start position P1 to the intermediate winding position P2 side.

Therefore, in the wound guide wire 100, due to the tensile force of the operator, the arc formed along the circumferential direction R in which the winding axis M is the central axis decreases, and the guide wire 100 moves from the winding start position P1 side to the intermediate winding position P2 side.

In addition, in the inner wall 11, the wall surface from one end portion 11a thereof to the other end portion 11b is bent in a convex shape toward the winding axis M side. Therefore, in a region leading from the winding start position P1 up to the intermediate winding position P2, the guide wire 100 smoothly moves while coming into sliding contact with the bent wall surface of the inner wall 11. In this state, the operator winds all of the guide wire 100 around the inner wall 11.

Furthermore, if the operator releases the hand from the guide wire 100, the guide wire 100 held at the intermediate winding position P2 attempts to return to the original position due to the elastic force. In this manner, the arc formed along the circumferential direction R in which the winding axis M is the central axis increases, and the guide wire 100 is guided to the outer wall 12 side. Therefore, the guide wire 100 moves from the intermediate winding position P2 to a winding end position P3 on one end portion 12a side of the outer wall 12. Here, the interlock wall 13 extends so as to be further separated from the inner wall 11 than the portion on the line (portion of Q-Q illustrated in FIG. 3) connecting one end portion 11a of the inner wall 11 and one end portion 12a of the outer wall 12 to each other. That is, in a region leading from the intermediate winding position P2 up to the winding end position P3, the guide wire 100 can smoothly move without coming into contact with the interlock wall 13.

Furthermore, the guide wire 100 moving to the winding end position P3 stays at the place. Here, in the outer wall 12, the wall surface from one end portion 12a thereof to the other end portion 12b is bent in a convex shape toward a side separated from the winding axis M. Therefore, even if due to the resilience generated when the guide wire 100 comes into contact with the outer wall 12 after being separated from the inner wall 11, the guide wire 100 arriving at the winding end position P3 is vertically moved along the winding axis M while coming into contact with the wall surface of the outer wall 12, or even if the guide wire 100 is temporarily separated from the wall surface of the outer wall 12, the guide wire 100 is finally guided to a bent central portion of the outer wall 12, and stays in the central portion.

In addition, due to the elastic force of the guide wire 100 itself, the guide wire 100 arriving at the winding end position P3 generates a frictional force between the outer peripheral surface of the guide wire 100 and the outer wall 12, and is fixed inside the accommodation space 14. Therefore, without using a specific fixing tool, the accommodation tool 10 according to the embodiment can fix the guide wire 100 so as not to be untied from the accommodation space 14. From this viewpoint, it is preferable that the medical elongated body to be accommodated in the accommodation tool 10 according to the embodiment has the elastic force.

Next, as illustrated in FIG. 6, the guide wire 100 accommodated in the accommodation tool 10 is brought into a wet state.

In accordance with an exemplary embodiment, the operator soaks the accommodation tool 10 having the wound guide wire 100 in the vat 200. The vat 200 is filled in advance with a physiological salt solution 300. The physiological salt solution 300 permeates the accommodation space 14 of the accommodation tool 10 from the through-hole 13e open on the interlock wall 13, the gap 12d of the outer wall 12, or a portion between the outer wall 12 and the inner wall 11, thereby bringing the guide wire 100 into the wet state. While the guide wire 100 is introduced again into a living body after being removed once from the inside of the living body, the guide wire 100 is soaked in the physiological salt solution 300 filling the vat 200, thereby maintaining the wet state. When the operator introduces the guide wire 100 again into the living body, the operator removes the accommodation tool 10 from the vat 200.

Next, a method of removing the guide wire 100 accommodated in the accommodation tool 10 outward when the operator introduces the guide wire 100 again into the living body will be described with reference to FIGS. 7 and 8.

As illustrated in FIG. 7, the operator grips an end portion (for example, a distal side) of the guide wire 100 through the gap 12d of the outer wall 12 of the accommodation tool 10, and pulls out the end portion straight in a tangential direction of the circumferential direction R. Here, when the operator pulls out the guide wire 100 from the accommodation tool 10, due to the tensile force, the arc formed along the circumferential direction R in which the winding axis M of the guide wire 100 is the central axis decreases. Therefore, the guide wire 100 whose arc decreases is separated from the winding end position P3 (the arc of the guide wire 100 at this position corresponds to r3 in the drawing) of one end portion 12a of the outer wall 12 illustrated in FIG. 8, and moves toward the inner wall 11 side. The guide wire 100 arrives at an unwinding position P4 (the arc of the guide wire 100 at this position corresponds to r4 in the drawing, r4<r3) located in the center of the accommodation space 14. Accordingly, a portion still in contact with the outer wall 12 can be prevented from being entangled with the guide wire 100.

In accordance with an exemplary embodiment, as illustrated in FIG. 7, the guide wire 100 is wound around the accommodation tool 10 multiple times. Accordingly, if the operator tries to pull out the guide wire 100, the whole body is pulled out sequentially one roll by one roll while being rotated in the circumferential direction R along the outer wall 12. In this case, the guide wire 100 of the pulled-out portion and the guide wire 100 of the portion not pulled out yet and rotating in the circumferential direction R along the outer wall 12 do not interfere with each other. In this way, the operator can smoothly pull out the guide wire 100 through the gap 12d. The operator introduces the guide wire 100 removed from the accommodation tool 10 into a catheter or the like.

Furthermore, as illustrated in FIG. 4 in addition to FIG. 7, the accommodation tool 10 utilizes flexibility of the guide wire 100. The guide wire 100 is wound around the inner wall 11 side, and is guided to the outer wall 12 side. In accordance with an exemplary embodiment, the guide wire 100 is not fixed to, or is not tightly wound around the inner wall 11 or the outer wall 12. Furthermore, when the operator pulls out the guide wire 100 from the accommodation tool 10, due to the tensile force of the operator, the arc formed along the circumferential direction R in which the winding axis M of the guide wire 100 is the central axis decreases. In this manner, the guide wire 100 moves to the accommodation space 14 side from the outer wall 12 side, and the guide wire 100 is unwound. In this way, the operator can easily remove the guide wire 100 from the accommodation tool 10.

In addition, according to the accommodation tool 10, only any guide wire 100 of a plurality of guide wires 100 accommodated together is moved from the outer wall 12 side to the accommodation space 14 side, while the tensile force of the operator is caused to decrease the arc formed along the circumferential direction R in which the winding axis M is the central axis. In this manner, the operator can easily remove the guide wire 100 without being entangled with the other guide wire 100.

In addition, in a case where the accommodation tool 10 has the plurality of outer walls 12 as illustrated in FIG. 7, the outer wall 12 is provided with a label for identifying the guide wire 100. In this manner, the guide wire 100 accommodated in the accommodation tool 10 can be easily identified from the guide wire 100 accommodated in the other accommodation tool. In accordance with an exemplary embodiment, for example, in a case where the plurality of guide wires 100 are accommodated together inside the accommodation tool 10, the operator provides the labels for respectively identifying the guide wires 100 for the outer walls 12 in which the end portions of the guide wires 100 are arranged. In this manner, the operator can easily identify the plurality of guide wires 100.

As described above, according to the accommodation tool 10 in the present embodiment, an operation effect is achieved by the following configurations.

In accordance with an exemplary embodiment, according to the accommodation tool 10, the other end portion 11b extending from one end portion 11a of the inner wall 11 extends in the stretching direction intersecting the radial direction so as to be longer than the other end portion 12b extending from one end portion 12a of the outer wall 12, and tilts toward the outer wall 12. According to this configuration, if the operator winds the guide wire 100 from the other end portion 11b side of the inner wall 11, the guide wire 100 is wound without being interfered with the other end portion 12b of the outer wall 12. Due to the tensile force, the arc formed along the circumferential direction R decreases. After the guide wire 100 moves from the other end portion 11b side of the inner wall 11 to one end portion 11a side, the elastic force causes the guide wire 100 to return to the original position in a state where the guide wire 100 is wound. In this manner, the arc formed along the circumferential direction R increases, and the guide wire 100 is guided to the outer wall 12 side. Therefore, the operator can easily wind and accommodate the flexible guide wire 100 in the accommodation tool 10. In addition, when the guide wire 100 is pulled out from the accommodation tool 10 according to the embodiment, the guide wire 100 is successively moved close to the inner wall due to the tension generated in the guide wire 100. In this manner, the guide wire 100 can be easily removed from the accommodation tool 10 without being entangled inside the accommodation tool 10. In addition, in a case where the plurality of guide wires 100 are accommodated in the accommodation tool, the same advantageous effect can also be expected.

Furthermore, according to the accommodation tool 10, the other end portion 12b of the outer wall 12 tilts toward the inner wall 11. Therefore, when the guide wire 100 is wound around the inner wall 11 by the operator attempts to return to the original position due to the elastic force and the arc formed along the circumferential direction R increases, the guide wire 100 is guided from the other end portion 12b side of the outer wall 12 to one end portion 12a side. Therefore, the guide wire 100 can be reliably accommodated without being separated to the outside.

Furthermore, according to the accommodation tool 10, the terminal of the other end portion 11b of the inner wall 11 is located further outward in the radial direction than the terminal of the other end portion 12b of the outer wall 12. Therefore, when the guide wire 100 wound around the inner wall 11 by the operator attempts to return to the original position due to the elastic force and the arc formed along the circumferential direction R increases, even if the guide wire 100 moves in the stretching direction intersecting the radial direction, the movement of the guide wire 100 is restricted by the inner wall 11 disposed so as to cover the outer wall 12. Therefore, the guide wire 100 can be sufficiently accommodated without being separated to the outside.

Furthermore, according to the accommodation tool 10, in the inner wall 11, the wall surface from one end portion 11a to the other end portion 11b is bent inward in the radial direction in a convex shape. Therefore, in the guide wire 100 wound around the inner wall 11 by the operator, when the arc formed along the circumferential direction R decreases due to the tensile force applied by the operator and the guide wire 100 moves from the other end portion 11b of the inner wall 11 side to one end portion 11a side, the guide wire 100 can be smoothly moved on the bent wall surface. That is, the accommodation tool 10 can prevent the guide wire 100 from being caught on the wall surface of the inner wall 11.

In addition, the interlock wall 13 extends so as to be further separated from the inner wall 11 or the outer wall 12 than the portion on the line connecting one end portion 11a of the inner wall 11 and one end portion 12a of the outer wall 12 from each other. Therefore, when the guide wire 100 wound around the inner wall 11 by the operator attempts to return to the original position due to the elastic force, the arc formed along the circumferential direction R increases, and the guide wire 100 is guided to the outer wall 12 side, the guide wire 100 can be smoothly moved without being brought into contact with the interlock wall 13.

In addition, in the outer wall 12, the wall surface from one end portion 12a to the other end portion 12b is bent outward in the radial direction in a convex shape. Therefore, the guide wire 100 which attempts to return to the original position due to the elastic force and whose arc increases, even if due to the resilience generated when the guide wire 100 comes into contact with the outer wall 12 after being separated from the inner wall 11, the guide wire 100 is vertically moved along the stretching direction intersecting the radial direction while coming into contact with the wall surface of the outer wall 12, or even if the guide wire 100 is temporarily separated from the wall surface of the outer wall 12, the guide wire 100 can be finally guided to the bent central portion of the outer wall 12, and can be sufficiently accommodated.

Furthermore, the accommodation tool 10 has the plurality of outer walls 12 formed by leaving the gap 12*d* therebetween along the circumferential direction R. Therefore, the operator can pull out the guide wire 100 accommodated between the inner wall 11 and the outer wall 12 from the gap 12*d*. That is, it is not necessary to pull out the guide wire 100 from the other end portion 11*b* side of the inner wall 11 by tilting the guide wire 100 in the stretching direction intersecting the radial direction. The guide wire 100 can be smoothly pulled out along the circumferential direction R.

Furthermore, the accommodation tool 10 has the plurality of inner walls 11. In accordance with an exemplary embodiment, the plurality of inner walls 11 have the gap between the adjacent inner walls 11. The outer wall 12 faces the gap formed between the adjacent inner walls 11 by leaving the accommodation space 14 therebetween. Therefore, according to the accommodation tool 10, since the plurality of inner walls 11 and outer walls 12 interlock with the interlock wall 13, it is possible to maintain sufficient strength. Furthermore, the operator can visually confirm the proximal side or the distal side of the guide wire 100 wound around the accommodation tool 10 via the gap in many directions. Accordingly, when the guide wire 100 is pulled out from the accommodation tool 10, the operator is likely to search for the proximal side or the distal side.

Furthermore, the accommodation tool 10 has the through-hole 13*e* on the interlock wall 13. Therefore, for example, when the guide wire 100 is soaked in the physiological salt solution 300 in order that the guide wire 100 is brought into a wet state by the physiological salt solution 300, the physiological salt solution 300 is likely to penetrate the guide wire 100 from the through-hole 13*e*. Furthermore, the accommodation tool 10 can be reduced in weight by the through-hole 13*e*. Furthermore, according to the accommodation tool 10, the accommodated guide wire 100 can be pulled out from the through-hole 13*e*. Furthermore, according to the accommodation tool 10, the accommodated guide wire 100 can be visually confirmed from the through-hole 13*e*.

Furthermore, the accommodation tool 10 can include the space between the other end portion 11*b* of the inner wall 11 and the other end portion 12*b* of the outer wall 12. Therefore, the operator is likely to grip the accommodation tool 10 by inserting his or her fingertip into the space and pinching the inner wall 11 and the outer wall 12.

Hitherto, the accommodation tool 10 according to the present disclosure has been described with reference to the embodiment. However, without being limited to only the configurations described with reference to the embodiment, the present disclosure can be appropriately modified within the scope described in the appended claims.

For example, the accommodation tool 10 according to the present disclosure is configured so that the guide wire 100 wound around the inner wall 11 attempts to return to the original position due to the elastic force, the arc increases, and the guide wire 100 comes into contact with the outer wall 12 after being separated from the inner wall 11. However, the present disclosure is not limited to this configuration. In some cases, even though the guide wire 100 is separated from the inner wall 11 by the elastic force of the guide wire 100, the guide wire 100 may stay in the accommodation space 14 and may not come into contact with the outer wall 12 until the guide wire 100 arrives at the outer wall 12.

In addition, the accommodation tool 10 according to the present disclosure is configured to wind and accommodate the guide wire 100. However, the present disclosure is not limited to this configuration. For example, the accommodation tool 10 according to the present disclosure may be configured to wind and accommodate a medical elongated body such as a catheter and a micro-tube.

In addition, the accommodation tool 10 according to the present disclosure is configured so that the proximal side of the medical elongated body starts to be wound while being fixed. However, the present disclosure is not limited to this configuration. The accommodation tool 10 according to the present disclosure may be configured so that the distal side of the medical elongated body starts to be wound while being fixed.

In addition, the accommodation tool 10 according to the present invention is configured so as to wind and accommodate the guide wire 100 in order that the guide wire 100 is brought into a wet state by the physiological salt solution. However, the present invention is not limited to this configuration. The accommodation tool 10 according to the present invention may be configured to wind and accommodate the medical elongated body in order to simply store the medical elongated body.

In addition, the accommodation tool 10 according to the present invention is configured to have an annular shape, since the guide wire 100 is wound and accommodated in an arc shape. However, the present invention is not limited to this configuration. The accommodation tool 10 according to the present invention may be configured to have a rectangular shape.

The detailed description above describes an accommodation tool, which winds and accommodates a flexible medical elongated body. The invention is not limited, however, to the precise embodiments and variations described. Various changes, modifications and equivalents can effected by one skilled in the art without departing from the spirit and scope of the invention as defined in the accompanying claims. It is expressly intended that all such changes, modifications and equivalents which fall within the scope of the claims are embraced by the claims.

What is claimed is:

1. An accommodation tool which winds and accommodates a flexible medical elongated body, the tool comprising:
   an inner wall around which the flexible medical elongated body is wound;
   an outer wall;
   an accommodation space configured to accommodate the flexible medical elongated body between the inner wall and the outer wall, and wherein the outer wall is disposed further outward in a radial direction from a centroid of the accommodation tool than the inner wall;
   an interlock wall configured to interlock the inner wall to the outer wall; and
   wherein the inner wall extends in a direction intersecting the radial direction so as to be longer than the outer wall, and wherein the inner wall tilts toward the outer wall.

2. The accommodation tool according to claim 1, wherein the outer wall tilts toward the inner wall.

3. The accommodation tool according to claim 1, wherein a terminal of the inner wall is located further outward in the radial direction than a terminal of the outer wall.

4. The accommodation tool according to claim 1, further comprising:
a wall surface of the inner wall being bent inward in the radial direction in a convex shape;
the interlock wall extends so as to be further separated from the inner wall or the outer wall than a portion on a line connecting the inner wall and the outer wall from each other; and
wherein a wall surface of the outer wall is bent outward in the radial direction in a convex shape.

5. The accommodation tool according to claim 1, wherein the outer wall comprises a plurality of outer walls, each of the plurality of outer walls having a gap between adjacent outer walls along a circumferential direction of the plurality of outer walls.

6. The accommodation tool according to claim 5, wherein the inner wall comprises a plurality of inner walls, each of the plurality of inner walls having a gap between adjacent inner walls along the circumferential direction of the plurality of the inner walls; and
wherein each of the plurality of outer walls are arranged in the gap between the adjacent inner walls.

7. The accommodation tool according to claim 1, further comprising:
a through-hole formed on the interlock wall.

8. The accommodation tool according to claim 1, further comprising:
a space between the inner wall and the outer wall.

9. An accommodation tool which winds and accommodates a flexible medical elongated body, the tool comprising:
an inner wall around which the flexible medical elongated body is wound;
an outer wall;
an accommodation space configured to accommodate the flexible medical elongated body between the inner wall and the outer wall, and wherein the outer wall is disposed further outward in a radial direction from a centroid of the accommodation tool than the inner wall;
an interlock wall configured to interlock the inner wall to the outer wall;
wherein the inner wall extends in a direction intersecting the radial direction so as to be longer than the outer wall, and the inner wall tilting toward the outer wall;
the outer wall tilting toward the inner wall; and
a terminal of the inner wall is located further outward in the radial direction than a terminal of the outer wall.

10. The accommodation tool according to claim 9, further comprising:
a wall surface of the inner wall being bent inward in the radial direction in a convex shape;
the interlock wall extending so as to be further separated from the inner wall or the outer wall than a portion on a line connecting the inner wall and the outer wall from each other; and
a wall surface of the outer wall being bent outward in the radial direction in a convex shape.

11. The accommodation tool according to claim 9, wherein the outer wall comprises a plurality of outer walls, each of the plurality of outer walls having a gap between adjacent outer walls along a circumferential direction of the plurality of outer walls; and
wherein the inner wall comprises a plurality of the inner walls, each of the plurality of the inner walls having a gap between adjacent inner walls, and wherein the adjacent outer walls are arranged in the gap between the adjacent inner walls.

12. The accommodation tool according to claim 9, further comprising:
a through-hole formed on the interlock wall; and
a space between the inner wall and the outer wall.

13. A method of winding a flexible medical body around an accommodation tool, the accommodation tool including an inner wall, an outer wall, an accommodation space configured to accommodate the flexible medical elongated body between the inner wall and the outer wall, and wherein the outer wall is disposed further outward in a radial direction from a centroid of the accommodation tool than the inner wall, and an interlock wall configured to interlock the inner wall to the outer wall, wherein the inner wall extends in a direction intersecting the radial direction so as to be longer than the outer wall, and wherein the inner wall tilts toward the outer wall, the method comprising:
winding the flexible medical elongated body around the inner wall of the accommodation tool while pulling on the flexible elongated body.

14. The method according to claim 13, comprising:
when starting to wind the flexible medical elongated body around the accommodation tool, pushing on an end portion of the flexible medical elongated body to prevent the movement of the end portion of the flexible medical elongated body.

15. The method according to claim 14, comprising:
releasing the end portion of the flexible medical elongated body after winding the flexible medical elongated body around the inner wall of the accommodation tool.

16. The method according to claim 15, wherein upon releasing the flexible medical elongated body, the flexible medical elongated body attempts to return to an original position due to an elastic force; and
forming an arc formed along a circumferential direction R in which a winding axis M is a central axis increases, and guiding the flexible medical elongated body to the outer wall side after being separated from the inner wall.

17. The method according to claim 16, comprising:
gripping the accommodation tool and pushing on the outer wall of the accommodation tool; and
winding the flexible medical elongated body around the inner wall by pinching the flexible medical elongated body.

18. The method according to claim 17, comprising:
placing the accommodation tool having the wound flexible medical elongated body in a vat filled with a physiological salt solution.

19. The method according to claim 18, comprising:
removing the accommodation tool from the vat; and
gripping the end portion of the wound flexible medical elongated body guide through the gap of the outer wall of the accommodation tool, and pulling out the end portion straight in a tangential direction of the circumferential direction.

20. The method according to claim 19, comprising:
introducing the unwound flexible medical elongated body into a catheter.

* * * * *